(12) United States Patent
Joensuu et al.

(10) Patent No.: US 9,304,120 B2
(45) Date of Patent: Apr. 5, 2016

(54) METHOD AND SYSTEM FOR ANALYZING A LIQUID SAMPLE CONTAINING PARTICLES OF SOLID MATTER AND THE USE OF SUCH A METHOD AND SYSTEM

(71) Applicant: Kemira, Helsinki (FI)

(72) Inventors: Iiris Joensuu, Espoo (FI); Marjatta Piironen, Espoo (FI)

(73) Assignee: Kemira Oyj, Helsinki (FI)

( * ) Notice: Subject to any disclaimer, the term of this patent is extended or adjusted under 35 U.S.C. 154(b) by 101 days.

(21) Appl. No.: 14/088,403

(22) Filed: Nov. 24, 2013

(65) Prior Publication Data

US 2015/0147814 A1   May 28, 2015

(30) Foreign Application Priority Data

Nov. 24, 2013   (FI) .................................... 20136172

(51) Int. Cl.
*G01N 33/34* (2006.01)
*G01N 21/85* (2006.01)
*G01N 15/02* (2006.01)
*G01N 15/00* (2006.01)

(52) U.S. Cl.
CPC .......... *G01N 33/343* (2013.01); *G01N 15/0255* (2013.01); *G01N 15/0272* (2013.01); *G01N 21/85* (2013.01); *G01N 2015/0053* (2013.01)

(58) Field of Classification Search
CPC ................................................... G01N 33/34
USPC .................. 162/198, 263; 356/338; 422/68.1, 422/82.05, 82.08; 436/2, 172, 177, 183
See application file for complete search history.

(56) References Cited

U.S. PATENT DOCUMENTS

| | | | | |
|---|---|---|---|---|
| 828,963 | A * | 8/1906 | Peters et al. .................. | 209/458 |
| 2,976,997 | A * | 3/1961 | Miller ........................... | 209/454 |
| 3,802,964 | A * | 4/1974 | Forgacs et al. ............... | 162/263 |
| 3,884,750 | A * | 5/1975 | Iannazzi .......................... | 162/4 |
| 3,941,690 | A * | 3/1976 | Powers et al. ................. | 209/443 |
| 4,142,965 | A * | 3/1979 | Dolan .......................... | 209/487 |
| 4,276,119 | A * | 6/1981 | Karnis et al. ..................... | 162/49 |
| 4,342,618 | A * | 8/1982 | Karnis et al. .................... | 162/49 |
| 4,692,210 | A * | 9/1987 | Forrester .......................... | 162/49 |

(Continued)

OTHER PUBLICATIONS

Laitinen, O. et al, BioResources 2011, 6, 672-685.*

*Primary Examiner* — Arlen Soderquist
(74) *Attorney, Agent, or Firm* — Seppo Laine Oy

(57) ABSTRACT

The invention relates to a method and system for monitoring of particles properties in a stream and the use of such method and system. In particular, the invention concerns sampling of liquids like aqueous suspensions or filtrates that contain solid matter in forest industry, oil and mining industry, as well as in and water treatment, desalination or water reuse processes, and in subsequent measurement of the samples. A sample from a stream of liquid is dyed to stain particles contained in the sample, which is conducted to a first flow chamber having means for causing said sample to be divided into particle populations according to their size or mass. A liquid flow is applied through the first flow chamber to cause at least one particle population to flow into a second flow chamber. The particle populations are measured to produce at least one measurement signal representative of the amount and/or properties of the particles, and processing extract key variables of each particle population and presenting them as an analysis of particle populations or the whole sample in terms of a count and size of particles and/or their hydrophobicity.

18 Claims, 3 Drawing Sheets

(56) References Cited

U.S. PATENT DOCUMENTS

| | | | |
|---|---|---|---|
| 5,087,823 A * | 2/1992 | Silvy et al. | 250/573 |
| 5,296,375 A * | 3/1994 | Kricka et al. | 435/2 |
| 5,311,290 A * | 5/1994 | Olson et al. | 356/634 |
| 5,542,542 A * | 8/1996 | Hoffmann et al. | 209/17 |
| 5,617,955 A * | 4/1997 | Tanner | 209/458 |
| 5,785,182 A * | 7/1998 | Ashcraft | 209/44 |
| 6,010,593 A * | 1/2000 | Eymin Petot Tourtollet et al. | 162/4 |
| 6,156,270 A * | 12/2000 | Buechler | 422/417 |
| 6,311,550 B1 * | 11/2001 | Lehmikangas et al. | 73/61.71 |
| 7,674,355 B2 * | 3/2010 | Doshi et al. | 162/198 |
| 7,909,963 B2 * | 3/2011 | Di Cesare | 162/198 |
| 8,877,010 B2 * | 11/2014 | Saren | 162/198 |
| 2005/0155911 A1 * | 7/2005 | Loewen | 209/44 |
| 2008/0046127 A1 * | 2/2008 | Piironen et al. | 700/271 |
| 2008/0308241 A1 * | 12/2008 | Di Cesare | 162/162 |
| 2009/0032449 A1 * | 2/2009 | Mueth et al. | 210/94 |
| 2009/0084510 A1 * | 4/2009 | Perry et al. | 162/49 |
| 2009/0301674 A1 * | 12/2009 | Niinimaki et al. | 162/49 |
| 2011/0081674 A1 * | 4/2011 | Han et al. | 435/29 |
| 2011/0294187 A1 * | 12/2011 | Toner | 435/177 |
| 2013/0153510 A1 * | 6/2013 | Jansson et al. | 210/727 |
| 2013/0220922 A1 * | 8/2013 | Joensuu et al. | 210/632 |
| 2014/0174994 A1 * | 6/2014 | Bemate et al. | 209/155 |
| 2015/0114094 A1 * | 4/2015 | Vahasalo et al. | 73/61.71 |

* cited by examiner

METHOD AND SYSTEM FOR ANALYZING A LIQUID SAMPLE CONTAINING PARTICLES OF SOLID MATTER AND THE USE OF SUCH A METHOD AND SYSTEM

FIELD OF THE INVENTION

The invention comprises measurement and/or monitoring technology of industrial liquids containing solid matter. In particular, the invention concerns sampling of liquids like aqueous suspensions or filtrates that contain solid matter in forest industry, oil and mining industry, as well as in water treatment, desalination or water reuse processes, and in subsequent measurement of the samples. In more detail, the invention relates to an on-line analysis method and system utilizing fractionation technology of a sample flow.

BACKGROUND OF THE INVENTION

An example of a remarkable area where measurements of solid matter containing liquids is needed is forest industry, in which wood pulp samples or filtrates, such as e.g. wire water, white water, thickener filtrates or another similar pulp filtrate, or circulated water, need to be monitored in order to be able to control the overall process. E.g. in oil and mining industry processes and in water treatment industry, like water reuse, desalination processes and cooling water treatment, the liquids used often contain solid matter that need to be measured and monitored.

Such processes can be carried out off-line or on-line, where off-line methods often involve batch sampling and laboratory analyses. They have the benefit of providing accurate and versatile information on the suspension but suffer from considerable time delays. On-line methods, on the other hand, provide instant or almost instant information on the suspension, but the data that can be obtained is usually not as accurate as can be achieved in the laboratory. Some suspension properties cannot be measured using present on-line techniques.

Many such suspensions include particles, whose amount and size distribution have a considerable effect on upcoming process stages. E.g. agglomeration has, in fact, been shown to be the main threat for deposition and related running problems on paper machines. Liquids and filtrates in pulp industry also have a strong tendency to flocculate, which makes the analysis of the solid matter in liquid streams challenging.

Some prior art pulp sample or filtrate monitoring techniques have utilized sample fractionation e.g. by filtration, centrifugation, sedimentation or column flow. The only known continuous fractionator is a column flow fractionator, also called a "tube fractionator". Tube fractionators are discussed e.g. in WO 2007/122289 and WO 2010/116030.

So-called flow cytometry technique has proved to be successful in detecting and assessing e.g. particle counts, size and/or type in pulp samples or filtrates originating from pulp and paper making industry. However, that technique requires manual sample pre-treatment in the laboratory and cannot be used for online measurements. Other known techniques discussed e.g. in WO 2012/010744 and WO 2012/010745 provide on-line information on the overall turbidity of samples. However, that information is not sufficient for all process control needs as the methods cannot differentiate different types of particles based, e.g. on hydrophobicity, particle size, and/or nature of the particles, whereby no detailed information is provided on disturbing substances.

Field flow fractionation (FFF) represents an approach in measurement of particles in non-industrial process samples. FFF was first described by J. C. Giddings in 1966 allows for physically separating particles having different physical properties from each other in a suspension. In principle, a flow of liquid is passed through a cell perpendicular to a field, e.g. a gravitation field, where smaller (lighter) particles move faster in the flow direction compared to larger (heavier) particles. Other fields that may be applied to the FFF cell include temperature and electricity.

In a flow cell, particles travel in a laminar flow and heavy particles sediment faster than light particles and therefore heavy particles experience extra friction upon touching the flow cell walls compared to light particles. There are many different FFF systems available depending on the application and most notably on the particle size range one wants to fractionate. For example, there are sedimentation FFF (Sd-FFF) systems available where the gravitational field is induced through centrifugal force.

It is however typical that an SdFFF system is only capable of handling very small quantities of sample, which is not applicable in a paper mill sample, if turbidity is used as the primary detector. The main problem with samples originating from industrial processes, e.g. with paper mill samples is the presence of fibers and especially fiber fines that have a strong tendency to flocculate in the FFF cell and thus block the cell. This makes the fractionation challenging as the flocks entrap also light particles.

In addition to flocculation, another problem is the mechanical or chemical sticking of substances to each other and attaching of stickies and hydrophobic substances to surfaces of known fractionation systems, in particular those based on cross-flow filters or known FFF techniques.

One technique for analyzing papermaking process samples is a method where harmful and uncontrolled agglomeration of pitch, stickies, scale, microbes and slime that disturb the papermaking process causing production down-time and paper defects are detected. The core of the system is the fractionation of particles according to their mass and/or size. The fractionated samples are analyzed with optical measurements.

The system is based on the Finnish patent application No. 20125560, filed by the present applicant, and is based on field flow fractionation, where the fractionating is performed by conducting the sample to a disintegration channel that one or more depressions, and by applying a liquid flow having a non-constant temporal velocity profile through the disintegration channel. In this way, solid matter of the sample will gradually be taken with the liquid flow from the depressions for providing sample fractions. This approach allows for measuring the particle size and/or mass distribution of a filtrate or a pulp sample and has proved to detect paper machine problems that cannot be seen with traditional measurements. There is no limitation as to the particle sizes that can be detected and measured, unlike many laboratory methods that work in the micron range.

The present invention seeks to further develop this and similar systems by developing a robust on-line system for continuous monitoring of hydrophobic/hydrophilic particles in water streams and pulp suspensions. Means of interpreting the results and to extract key variables for particle counts and hydrophobicity of a sample is also disclosed. Pre-treatment and separation of samples in order to achieve the objectives is described.

SUMMARY OF THE INVENTION

The present invention is directed to a system and a method of analyzing a liquid sample containing particles of solid matter, where the analysis is done on-line by collecting a sample from a stream of liquid, and a dye is added to the sample to stain the particles contained therein. The sample can be fractionated, pretreated or untreated. Thus, the particles in the sample can be separated into different particle populations, the separation being carried out by fractionation, or by settling or centrifugation, e.g. according to the mass or size (or both) of the particles.

According to an embodiment of the invention, the sample is conducted to a first flow chamber equipped with disintegration means, where a liquid flow of water is introduced with a velocity profile which causes fractioning of the sample particles into to one or several particle populations. Initially a low velocity is used, causing smaller or lighter particle populations to passes the disintegration means first, and by gradually, e.g. stepwise, increasing the liquid flow velocity according to the velocity profile, all particle populations will pass the disintegration means at a retention time characteristic for the properties of each population. The particle populations flow into a second flow chamber having an essentially laminar flow, at which at least one physical or chemical property of the stained particles in a particle population is measured with optical instruments and/or detectors, in order to produce at least one measurement signal. The measurement signals are processed for each measured particle population to extract key variables descriptive of the measured properties, and to correlate measurements of individual populations to other parameters of the process and/or to key variables of the whole sample. The chemical or physical properties of the sample to be measured may be one or more of the following: concentration of particles, volume of particles, surface area of particles, particle size, turbidity, concentration of suspended solid, light absorbance, fluorescence, light scattering, and hydrophobicity.

The invention offers significant advantages, as it allows for measurement of particle counts and hydrophobicity for each population by using optical sensors/measurements like light scattering, particle counter, turbidity, absorbance, fluorescence, and suspended solids. This provides for the design of a robust and simple online system. In contrast to existing solutions, each particle need not be the analyzed one by one.

The invention is also directed to the use of an inventive method in a system for analyzing a liquid sample containing particles of solid matter.

The details of the various embodiments of the invention are explained below and set forth in the appended claims. Next, embodiments and advantages of the invention are described in more detail with reference to the attached drawings.

DETAILED DESCRIPTION OF EMBODIMENTS

Figure 1:
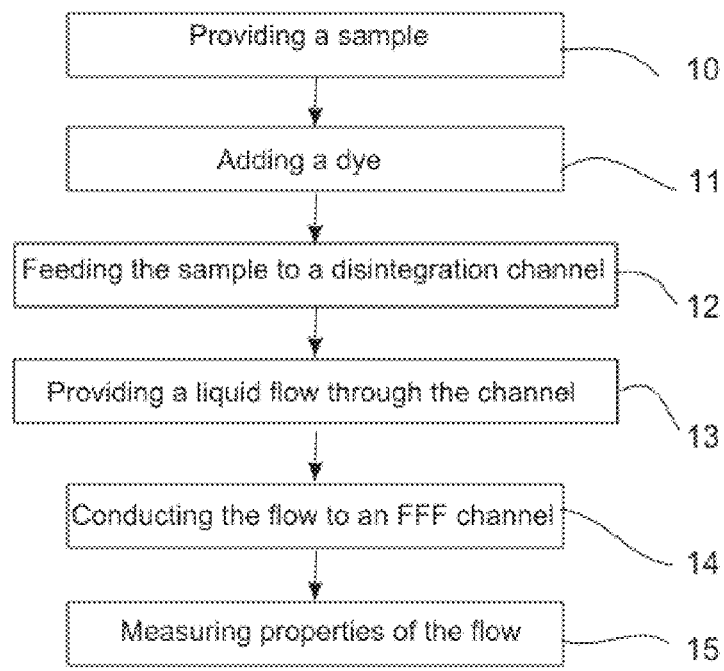
FIG. 1 shows a flow chart of the method according to one embodiment of the present invention.

With reference to FIG. 1, according to one embodiment, the present method comprises a sequence of several phases. In phase 10, a sample is provided directly from a process to be monitored or controlled. Typically, the sample is a batch sample or "plug" of about 10 ml taken with automated sampling means. Next, in phase 11, a hydrophobic dye like Nile red is used to stain the sample. In this pre-treatments stage the particles are prepared for the measurement. The staining of the sample or particles of the sample is done before or in the disintegration channel, i.e. during fractionation. The amount of stain may be around 40 µl per milliliter of sample.

In phase 12 the sample is fed to a disintegration channel. It is preferred to drive the sample relatively fast to the channel so that it experiences rapid local accelerations which break potential flocks in the sample. The sample should however not be fed with a velocity making it pass the disintegration channel. The sample is to be retained in its entirety in the disintegration channel until the start of the next phase.

In phase 13, a liquid flow, typically water flow, is conducted through the disintegration channel to a field flow fractionation channel (FFF) with essentially laminar flow properties. The overall dilution of the sample in water may be around 1:10-1:200, preferably around 1:50-1:70. This phase is denoted with the reference numeral 14. In order to separate the smallest particles from the larger or heavier ones, the flow velocity is low at the beginning. In this way particle separation is achieved in channel with light particles passing the system first. In order to get heavier particles into the water flow, flow velocity is increased step by step. The velocity is thus increased to a level which catches even the heaviest (or at least all of interest) particles. As a consequence, the sample is effectively fractionated in the FFF channel at step 14. The flow velocity profiles may preferably are optimized for different types of liquids, for example one for paper machine white water samples and another for pulp samples.

The desired properties of the fractionated sample are measured in phase 15. According to the invention, at least optical measurements are performed, but there may be also alternative or additional measurement stages.

The disintegration and fractionation phases 13 and 14, and typically also the measurement phase 15, occur at least partly simultaneously in a continuous configuration. However, it is also possible to recover the fractions for subsequent separate measurements, if immediate on-line results are not needed.

The whole fractionation process may take about 50 minutes, including sample measuring and cleaning of the sampling system. Of course there may be variation in the time cycle depending on the system and nature of the sample, for example, 2-180 minutes, or typically 5-50 minutes.

Figure 2:
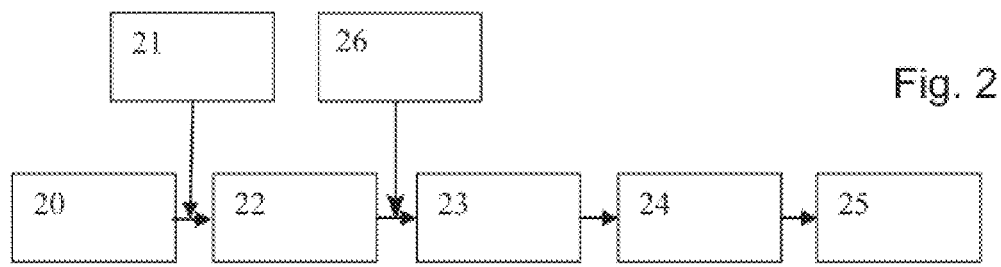
FIG. 2 shows a block diagram of various elements of the present measurement system according to one embodiment.

With reference to FIG. 2, according to one embodiment, the measurement system comprises a fractionator part 20, 21, 22, 23, 24, 26 and a measurement part 25 with one or more detectors. The fractionator part comprises a source of fresh water 20 and a sample-taking device 21. A pump 22 is provided for driving the sample or water forward in the system using suitable valves (not shown). The pump is connected in forward direction to a first flow chamber, here a disintegration channel 23 and further to a second flow chamber, here a field flow fractionating (FFF) channel 24. A staining unit 26 with a dye reservoir (not shown) feed the appropriate amount of dye to the sample before fractioning the particles into populations. The system also includes a processing unit having e.g. a programmable logic (PLC) or industrial computer for automatic operation of the system and data collection. The processing unit may also include a computer having appropriate software to carry out the processing of the measurement signals to extract the key variables which are the main deliverables of the system. The computer may be included in the measurement part 25, or be plugged into it as a separate computer, optionally for remote monitoring (not shown). An automatic cleaning system for the various liquid-carrying parts of the system may also be provided.

Figure 3:
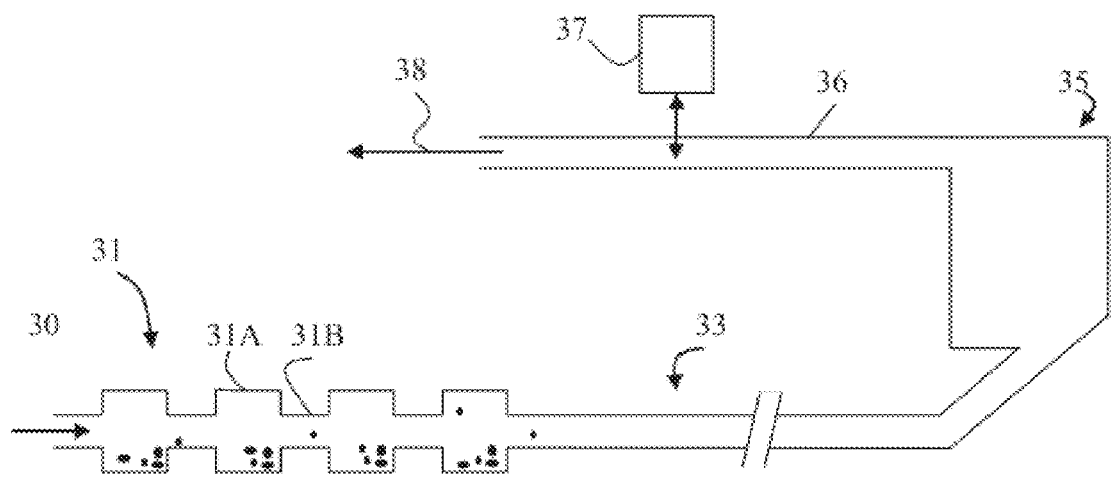
FIG. 3 shows a schematic illustration of a measurement system according to one embodiment of the invention.

In FIG. 3 there is shown in a more illustrative schematic view of the system of FIG. 2. Sample and water input stream is denoted with the numeral 30 and output stream with numeral 38. The exemplary disintegration channel 31 is provided with expansions 31A and narrow parts 31B such that depressions are formed to the region of the expansion 31A. The depressions serve to disintegrate the flocs and to gradually release particles according to their size and/or mass to the FFF channel 33 following the disintegration channel 31. The fractionation proceeds in the FFF channel 33. A homogenizer tube 35, which is an optional part, comprises a vessel with a larger cross-sectional area than the FFF channel 33 and homogenizes the particle populations and flocs exiting the FFF channel into one population. From the homogenizer tube 35, the fractionated sample is conducted via a conduit 36 to a measurement device 37, which is arranged to measure the desired physical and/or chemical property of the sample. The first flow chamber may without diverting from the inventive idea also be a fractionator of the type where particle separation into particle populations is based on particle settling, centrifugal separation or filtering according to the mass or size (or both) of the particles. Also, the sample may be fractionated as pretreated or untreated.

Figure 4:
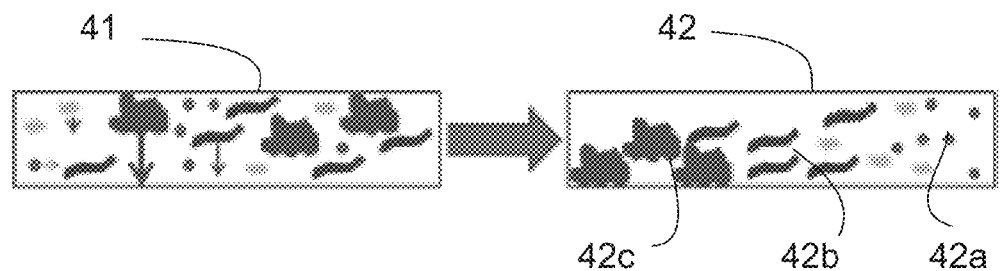
FIG. 4 shows the principle of field flow fractionation.

Referring to FIG. 4, where a typical sample before and after fractionating is shown. The un-fractioned sample 41 contains, of course, a mix of particles of different sizes. Heavier particles have a tendency to sink, as shown by the arrows pointing downwards in 41. In a filed flow fractioned sample 42, the particles are divided into (at least) three particle populations 42a-42b in an FFF channel, as shown. In reality, the distance between the populations in the FFF channel is larger than in the picture because the sample is at this stage diluted with water as described in earlier. It can be seen that there is both a horizontal and vertical separation of the particle populations, the vertical difference being due to the difference in weight of the particles. The present method is aimed for monitoring particles, e.g. colloids, stickies, wood pitch, white pitch, flocs, fibers and agglomerated particles.

Figure 5:
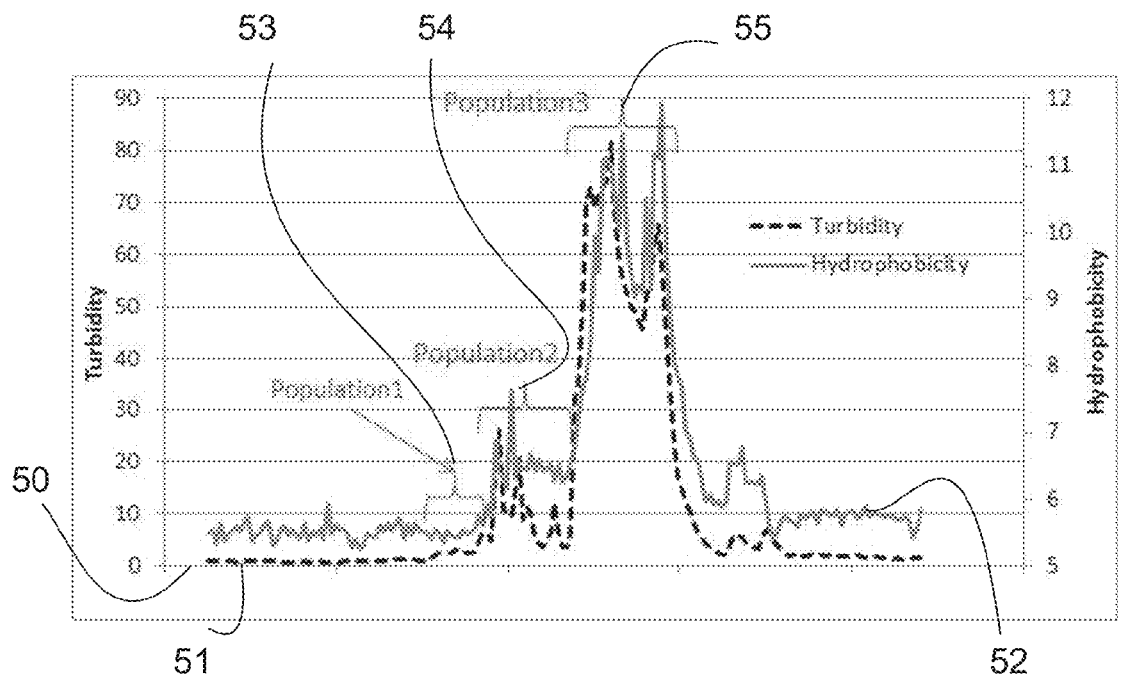
FIG. 5 shows fluorescence and turbidity signals.

The output signals of the online system are fluorescence intensity and turbidity. The fluorescence intensity correlates directly with hydrophobicity of the sample fractions when a hydrophobic dye like Nile red is added to the sample. Turbidity is used for measuring particle concentrations. It should be noted that the particle size and/or particle volume also affects turbidity. FIG. 5 shows an example of the turbidity signal 51 and hydrophobicity 52 for one wire water sample in a fine paper mill. 10 ml of sample was fed into the fractionator together with fresh dilution water. As can be seen, the turbidity first increases only slightly from the zero baseline 50 due to the small size and low concentration of particles. Small colloids in Population 1 (53) come out first from the fractionator, followed by population 2 (54) and heavier particles like agglomerates in population 3 (55), which come out from the fractionator when the flow velocity increases. As can be seen from FIG. 5, fluorescence starts to increase later than turbidity, which means that the smallest particles 53 are less hydrophobic than the larger ones 54, 55. The fluorescence intensity is quite high for the largest particles 55.

As can be seen, the inventive system produces data that is very useful and from where at least, the following key variables can be extracted from the data signals as shown in FIG. 5:

count(s) of particles: total count and count of each particle population
from the turbidity signal;

size(s) of particles
from the retention time of each particle populations in the system, i.e. the time when particles are exiting the fractionator;

particle size distribution
from turbidity and retention time(s);

hydrophobicity of particles: total hydrophobicity and hydrophobicity of each particle population
from the fluorescence signal;

hydrophobicity distribution of particles
from fluorescence signal and retention time(s).

A specific software toolkit is developed for signal pretreatment and calculation of key variables for the particle properties. Signal pretreatment includes here filtering, averaging, derivation and baseline correction of the signals. As an example of the procedure, the baseline may be removed from the raw signals of a fractionated sample, and the cumulative sums are calculated from signals. The cumulative sum of turbidity signal is correlated with the count of particles, and the cumulative sum of fluorescence signal is correlated with the hydrophobicity of the particles. Hydrophobicity and count for each particle population are derived from signals at certain time intervals. Each particle population has their own time interval in the second flow chamber. Total hydrophobicity and total count are derived from the whole signal of fractionated samples. The turbidity, particle size and number in a sample population may be determined by measuring absolute values or relative values. If relative measurement is used, the processing means for processing the measurement signal for each particle population is calibrated with regard to known samples.

In other words, key variables in a particle population are produced by means of calculating the cumulative sum of signal(s), derivation of signal(s), integral of signal(s), mean, maximum and minimum values of the signals or pretreated signals, in order to attach physical/chemical properties to each population. The chemical or physical properties of the sample to be measured may be one or more of the following: concentration of particles, volume of particles, surface area of particles, particle size, turbidity, concentration of suspended solid, light absorbance, fluorescence, light scattering, and hydrophobicity.

Optionally, a specific software toolkit contains means for calibration. Count of particles and/or size(s) of particles can be calibrated to SI-units using a suitable mathematical equation, e.g. first and/or second degree equations.

Optionally one or more key variables of individual populations or the whole sample are used for monitoring, controlling and/or optimization of a process (e.g. in a paper machine). Examples: key variables are used to monitor the running parameters and properties of a paper machine, including monitoring of agglomeration tendencies of particles in the process and, monitoring of chemical behavior in the process.

Optionally one or more key variables of individual populations or the whole sample are used for monitoring the performance of chemicals by controlling the chemicals (e.g. controlling the dosage of chemical) and optimization of chemical dosing or chemical program (type of chemicals, chemical dosages, dosing points of chemicals in the process).

Figure 6:
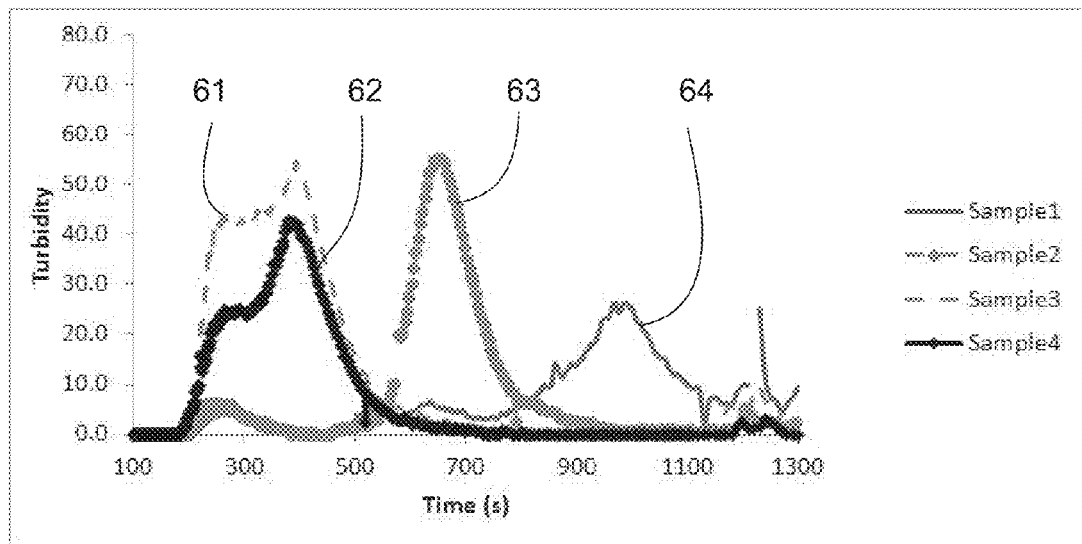
FIG. 6 shows turbidity profiles of wire water samples.
Figure 7:
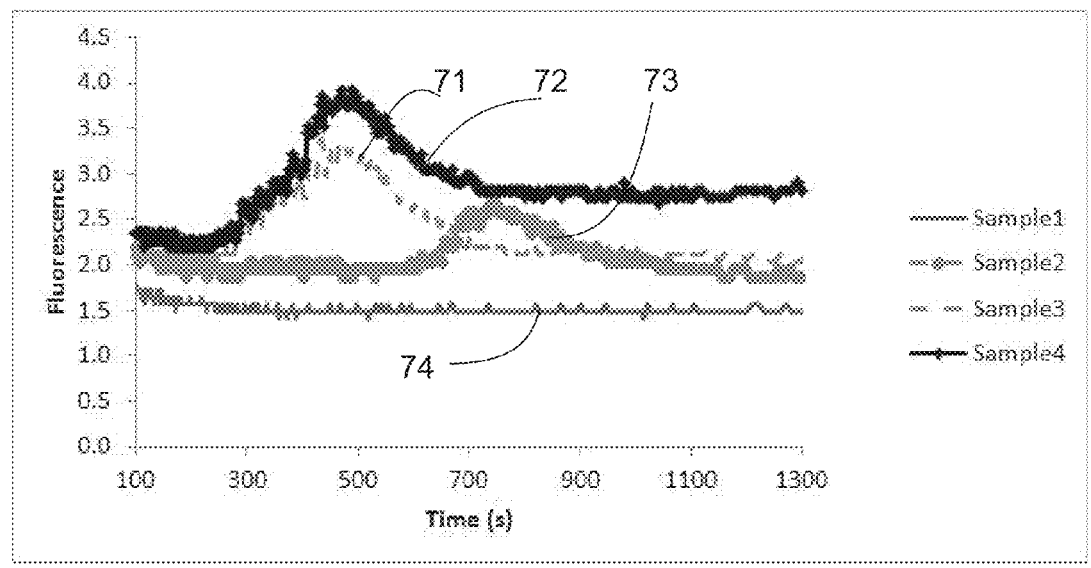
FIG. 7 shows fluorescence profiles of wire water samples.

In order to study hydrophobicity (fluorescence), size and count of particles in various environments, four wire water samples from different paper machines were measured with the inventive system equipped with turbidity and fluorescence sensors. The turbidity results presented in FIG. 6 show that the samples 61 and 62 have much smaller particles as compared with the sample 63 and the sample 64, which had very large agglomerates. The fluorescence profile of the same samples is shown in FIG. 7. The base line difference between the different profiles is most likely due to contamination of the fluorescence detector. The fluorescence results show that the samples 71, 72 containing mechanical pulp clearly have the highest fluorescence and therefore also hydrophobicity compared to samples 73 and 74. This is expected due to the presence of high amounts of wood pitch in these pulps. The most hydrophobic sample 72 also leaves the baseline much higher as compared to the starting baseline, indicating that such samples tend to contaminate the fluorescence detector, which is an important point when designing the washing cycles of an online instrument. Sample 74 does not show any fluorescence response at all.

In particular, the invention concerns sampling of liquids like aqueous suspensions or filtrates that contain solid matter in forest industry, oil and mining industry, as well as in and water treatment, desalination or water reuse processes, and in subsequent measurement of the samples. In more detail, the invention relates to an on-line analysis method and system utilizing fractionation technology of a sample flow.

The inventive technology is generic and can be widely applied in the pulp and paper industry, for example wet end monitoring, broke treatment, stickies control of recycled pulp and chemical/mechanical pulp treatment including bleaching and dry section.

It can be used for online monitoring of particle populations like colloids, white pitch, wood pitch, stickies, fines, fillers, or agglomerates, and their hydrophobicity. The inventive online system enables real-time problem solving and optimization of chemistry in a paper mill.

EXAMPLE

An inventive online system was used at a fine paper machine. The system measures particle properties in white water samples every 30 minutes. In order to get information of the particle hydrophobicity, the sample is stained with hydrophobic dye. The flow velocity profile of the system was optimized for this water. The system is able to separate the sample into at least four particle populations according to their size/mass (population 1-4). The experience from the mill test period indicates good repeatability.

The running problems (e.g. paper defects) in paper machine were linked to strong agglomeration of hydrophobic particles in the wet end. Therefore, the main target in this case was to monitor the counts and hydrophobicity of particle populations, especially agglomerates. The results achieved with the inventive system clearly indicate that the inventive approach works well. The inventive system can produce same type of data as laboratory equipment do, the main difference being that the system does not measure the exact values for each particle (size, count, hydrophobicity), but instead measures hydrophobicity and count values for the whole sample and for the detected particle populations. There is no limitation as to the particle sizes that can be detected and measured, unlike many laboratory methods that work in the micron range.

The inventive technology is generic and can be widely applied in the paper industry, including stickies control of recycled pulp and mechanical pulp treatment. It can be used for online monitoring of particle populations like colloids, fines, fillers, or agglomerates, and their hydrophobicity. The inventive online system enables real-time problem solving and optimization of chemistry in a paper mill.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A method of analyzing a liquid sample containing particles of solid matter, the method including the steps of:
   providing a sample from a stream of liquid;
   adding a dye to said sample to stain the particles contained therein;
   conducting the sample to a first flow chamber which includes a disintegration channel having one or more depressions;
   applying a liquid flow having a non-constant temporal velocity profile through said first flow chamber causing said sample to be divided into particle populations according to their size or mass;
   causing at least one particle population to flow into a second flow chamber;
   measuring by optical measurement at least one of said particle populations to produce at least one measurement signal representative of the amount and/or properties of the particles;

processing said measurement signal for each measured particle population to extract key variables of each particle population; and presenting said key variables as an analysis of particle populations or the whole sample in terms of a count and size of particles and/or their hydrophobicity.

2. A method according to claim 1, wherein the dye is a hydrophobic dye.

3. The method according to claim 1, wherein the first flow chamber is a fractionator.

4. A method according to claim 1, wherein the flow velocity in the first flow chamber disintegration channel is increased step by step according to said velocity profile, allowing smaller or lighter particle populations entering said second flow chamber having an essentially laminar flow first, and other particle populations later in an ascending order of size and weight, until all particle populations have entered said second flow chamber.

5. A method according to claim 1, wherein the first flow chamber is a fractionator where particle separation into particle populations is based on particle settling, centrifugal separation and/or filtering.

6. A method according to claim 1, wherein the amount and/or size of the particles in said sample is measured by light scattering of the particles in the sample.

7. A method according to claim 1, wherein the hydrophobicity of the particles in said sample is measured by measuring the fluorescence emitted by the particles in the sample.

8. A method according to claim 1, wherein the chemical or physical properties of said sample to be measured are one or more of the following: concentration of particles, volume of particles, surface area of particles, particle size, turbidity, concentration of suspended solid, light absorbance, fluorescence, light scattering, and hydrophobicity.

9. A method according to claim 8, wherein the processing of said measurement signals includes filtering, averaging and baseline correction of said signals.

10. A method according to claim 1, wherein the processing of said measurement signals for the key variables includes statistical operations on the data including one or more of the following: integration of signal(s), derivation of signal(s), cumulative sum of signal(s), mean value, maximum and minimum values.

11. A system for analyzing a liquid sample containing particles of solid matter, the system including:
means for providing a sample from a stream of liquid;
means or adding a dye to said sample;
a first flow chamber including a disintegration channel having one or more depressions for causing said sample to be divided into at particle populations determined by their size or mass;
means for applying a liquid flow having a non-constant temporal velocity profile through said first flow chamber;
a second flow chamber arranged to receive liquid containing at least one particle population from said first flow chamber;
optical measuring means for producing at least one measurement signal representative of the amount and/or character of the particles in said second flow chamber;
processing means for processing said measurement signal for each measured particle population to extract key variables of each particle population;
processing means for presenting said key variables as an analysis of particle populations or the whole sample in terms of a count and size of particles and/or their hydrophobicity.

12. A system according to claim 11, wherein the means for applying a liquid flow through said first flow chamber is arranged to increasing the liquid flow velocity in said first flow chamber stepwise according to a predetermined flow velocity profile.

13. A system according to claim 11, wherein the first flow chamber is a fractionator where particle separation into particle populations is based on particle settling, centrifugal separation or filtering.

14. A system according to claim 11, wherein the optical measuring means comprises means at said second flow chamber for measuring of light scattering of the particles in the sample.

15. A system according to claim 11, wherein the optical measuring means comprises means at said second flow chamber for measuring of fluorescence emitted by the particles in the sample.

16. A system according to claim 11, including processing unit having adapted for automatic operation of the sample taking, fractionating and data collection.

17. A system according to claim 11, including processing means for performing filtering, averaging and baseline correction of said measurement signals.

18. A system according to claim 11, including processing means for performing statistical operations on the key variables includes including one or more of the following: integration of signal(s), derivation of signal(s), cumulative sum of signal(s), mean value, maximum and minimum values.

* * * * *